US00PP20332P2

(12) United States Plant Patent
Sekiguchi et al.

(10) Patent No.: US PP20,332 P2
(45) Date of Patent: Sep. 22, 2009

(54) ***OSTEOSPERMUM* PLANT NAMED 'VIENT FLAMINGO'**

(50) Latin Name: *Osteospermum ecklonis*
Varietal Denomination: Vient Flamingo

(76) Inventors: Masayuki Sekiguchi, Kitashirota 497, Maebashi-city, Gunma 371-0055 (JP); Yoshihiro Hase, Ayugawa 475-1, Fujioka-city, Gunma 370-0078 (JP); Atsushi Tanaka, Kamikotori-machi 362-34, Takasaki-city, Gunma 370-0078 (JP)

( * ) Notice: Subject to any disclaimer, the term of this patent is extended or adjusted under 35 U.S.C. 154(b) by 0 days.

(21) Appl. No.: 12/152,677

(22) Filed: May 14, 2008

(51) Int. Cl.
*A01H 5/00* (2006.01)

(52) U.S. Cl. ..... Plt./360

(58) Field of Classification Search ..... Plt./360
See application file for complete search history.

*Primary Examiner*—Susan B McCormick Ewoldt
(74) *Attorney, Agent, or Firm*—C. A. Whealy

(57) ABSTRACT

A new and distinct cultivar of *Osteospermum* plant named 'Vient Flamingo', characterized by its compact, semi-upright, outwardly spreading and mounded plant habit; freely branching growth habit; freely flowering habit; large daisy-type inflorescences with yellow-colored ray florets with red purple-colored venation; and good garden performance.

2 Drawing Sheets

Botanical designation: *Osteospermum ecklonis.*
Cultivar denomination: 'Vient Flamingo'.

BACKGROUND OF THE INVENTION

The present invention relates to a new and distinct cultivar of *Osteospermum* plant, botanically known as *Osteospermum ecklonis,* and hereinafter referred to by the name 'Vient Flamingo'.

The new *Osteospermum* is a naturally-occurring whole plant mutation of the *Osteospermum ecklonis* 'Seikilrem', disclosed in U.S. Plant Pat. No. 13,407. The new *Osteospermum* was discovered and selected by the Inventors as a single flowering plant within a population of plants of 'Seikilrem' in a controlled greenhouse environment in Isegaki, Gunma, Japan in May, 2005.

Asexual reproduction of the new *Osteospermum* by terminal cuttings in a controlled environment in Isegaki, Gunma, Japan since January, 2007, has shown that the unique features of this new *Osteospermum* are stable and reproduced true to type in successive generations.

SUMMARY OF THE INVENTION

Plants of the new *Osteospermum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of the new *Osteospermum.* These characteristics in combination distinguish 'Vient Flamingo' as a new and distinct cultivar of *Osteospermum:*

1. Compact, semi-upright, outwardly spreading and mounded plant habit.
2. Freely branching growth habit.
3. Freely flowering habit.

4. Large daisy-type inflorescences with yellow-colored ray florets with red purple-colored venation.
5. Good garden performance.

Plants of the new *Osteospermum* differ from plants of the parent, 'Seikilrem', in the following characteristics:

1. Plants of the new *Osteospermum* have entire leaf margins whereas plants of 'Seikilrem' have serrated leaf margins.
2. Inflorescences of plants of the new *Osteospermum* and 'Seikilrem' differ in ray floret color as plants of 'Seikilrem' have bright yellow-colored ray florets.

Plants of the new *Osteospermum* can be compared to plants of the *Osteospermum* 'Seipepan', disclosed in U.S. Plant Pat. No. 16,213. In side-by-side comparisons conducted in Isegaki, Gunma, Japan, plants of the new *Osteospermum* differed from plants of 'Seipepan' in the following characteristics:

1. Plants of the new *Osteospermum* are not as upright as plants of 'Seipepan'.
2. Plants of the new *Osteospermum* had smaller leaves than plants of 'Seipepan'.
3. Plants of the new *Osteospermum* had entire leaf margins whereas plants of 'Seipepan' had serrated leaf margins.
4. Plants of the new *Osteospermum* had shorter, but broader ray florets than plants of 'Seipepan'.
5. Ray florets of plants of the new *Osteospermum* and 'Seipepan' differed in ray floret color as plants of 'Seipepan' had light orange-colored ray florets.

BRIEF DESCRIPTION OF THE PHOTOGRAPHS

The accompanying photographs illustrate the overall appearance of the new *Osteospermum.* These photographs show the colors as true as it is reasonably possible to obtain in colored reproductions of this type. Colors in the photographs may differ slightly from the color values cited in the detailed botanical description which accurately describe the colors of the new *Osteospermum.*

The photograph on the first sheet comprises a side perspective view of a typical flowering plant of 'Vient Flamingo' grown in a container.

The photograph on the second sheet is a close-up view of a typical inflorescence of 'Vient Flamingo'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in 15-cm containers in Toyota-city, Aichi, Japan during the late winter/early spring in a greenhouse and under conditions and practices which approximate those generally used in commercial *Osteospermum* production. Measurements and numerical values represent averages for typical flowering plants. Plants were pinched one time and were three months old when the photographs and description were taken. During the production of the plants, day temperatures ranged from 10° C. to 30° C., night temperatures ranged from 8° C. to 10° C. and light levels averaged 50,000 lux.

Botanical classification: *Osteospermum ecklonis* 'Vient Flamingo'.

Parentage: Naturally-occurring whole plant mutation of the *Osteospermum ecklonis* 'Seikilrem', disclosed in U.S. Plant Pat. No. 13,407.

Propagation:

*Type.*—Terminal vegetative cuttings.

*Time to initiate roots, summer.*—About 12 days at 25° C.

*Time to initiate roots, winter.*—About 20 days at 15° C.

*Time to produce a rooted young plant, summer.*—About 20 days at 25° C.

*Time to produce a rooted young plant, winter.*—About 27 days at 15° C.

*Root description.*—Fine, fibrous.

*Rooting habit.*—Freely branching.

Plant description:

*Plant form/growth habit.*—Compact, semi-upright, outwardly spreading and mounded plant habit. Inflorescences positioned well above the foliar plane. Moderately vigorous growth habit.

*Plant height.*—About 25 cm.

*Plant diameter.*—About 30 cm.

*Lateral branches.*—Quantity per plant: Freely branching habit, about 12 to 14 lateral branches per plant. Length: About 30 cm. Diameter: About 3.4 mm. Internode length: About 2 cm. Strength: Strong. Texture: Densely pubescent. Color: Close to 145A.

*Foliage description.*—Arrangement: Alternate, simple; sessile. Length: About 2.7 cm. Width: About 1.34 cm. Shape: Spatulate. Apex: Obtuse. Base: Attenuate. Margin: Entire. Texture, upper and lower surfaces: Smooth, glabrous; pubescence at the margins. Venation pattern: Pinnate. Color: Developing foliage, upper and lower surface: Close to 137A. Fully expanded foliage, upper surface: Close to 137A; midrib, close to 144B; lateral veins, close to 137B. Fully expanded foliage, lower surface: Close to 137B; venation, close to 143B.

Inflorescence description:

*Appearance.*—Daisy-type inflorescence form with ligulate to oblong-shaped ray florets. Inflorescences positioned above the foliage, arising from leaf axils. Disc and ray florets developing acropetally on a capitulum. Inflorescences face mostly upright. Freely flowering habit; about 20 inflorescences and inflorescence buds per plant. Inflorescences persistent. Inflorescences not fragrant.

*Flowering response.*—In Japan, plants of the new *Osteospermum* flower continuously throughout the spring. Early flowering habit, plants begin flowering about eight weeks after planting. Inflorescences last about one week on the plant.

*Inflorescence bud.*—Height: About 1.2 cm. Diameter: About 1.2 cm. Shape: Globular. Color: Close to 138A.

*Inflorescence size.*—Diameter: About 5.14 cm. Depth (height): About 2 cm. Disc diameter: About 7 mm. Receptacle height: About 1 cm. Receptacle diameter: About 1.7 cm.

*Ray florets.*—Length: About 2.6 cm. Width: About 6.5 mm. Shape: Ligulate to oblong. Apex: Broadly acute. Base: Attenuate. Margin: Entire. Texture, upper and lower surfaces: Smooth, glabrous; satiny. Orientation: Initially upright and with development, perpendicular to the peduncle. Number of ray florets per inflorescence: About 20 in a single whorl; ray florets imbricate. Color: When opening and fully opened, upper surface: Close to 10A; venation, close to 70B. When opening and fully opened, lower surface: Close to 153B.

*Disc florets.*—Length: About 7 mm. Diameter: Towards the apex, about 1.5 mm; towards the base, about 1 mm. Shape: Tubular with five lobes at the apex. Apex: Acute. Number of disc florets per inflorescence: About 74. Color, immature and mature: Apex: Close to 79A. Mid-section: Close to 155D. Base: Close to 149D.

*Phyllaries.*—Length About 1.2 cm. Width: About 2 mm. Shape: Lanceolate. Apex: Acute. Base: Fused. Margin: Entire. Texture, upper surface: Pubescent. Texture, lower surface: Smooth, glabrous. Quantity per inflorescence: About 17; phyllaries imbricate. Color, upper and lower surfaces: Close to 137B.

*Peduncles.*—Length, terminal peduncle: About 5 cm. Length, fourth peduncle: About 1.5 cm. Diameter: About 2 mm. Strength: Strong. Texture: Pubescent. Orientation: Terminal peduncle, erect; lower peduncles, about 45° to 60° from vertical. Color: Close to 145A.

*Reproductive organs.*—Androecium: Present on disc florets only. Filament length: Less than 1 mm. Anther shape: Oblong. Anther length: About 1 mm. Anther color: Close to 103A. Pollen amount: Scarce. Pollen color: Close to 23A. Gynoecium: Present on ray florets only. Pistil length: About 7 mm. Stigma color: Close to 77A. Style length: About 5 mm. Style color: Close to 83D. Ovary color: Close to 145A.

*Seeds/fruit.*—Seed and fruit development have not been observed.

Disease/pest resistance: Plants of the new *Osteospermum* have not been shown to be resistant to pathogens and pests common to *Osteospermums*.

Garden performance: Plants of the new *Osteospermum* have been observed to have good garden performance and to tolerate rain, wind and temperatures ranging from about 5° C. to about 35° C.

It is claimed:

1. A new and distinct *Osteospermum* plant named 'Vient Flamingo' as illustrated and described.

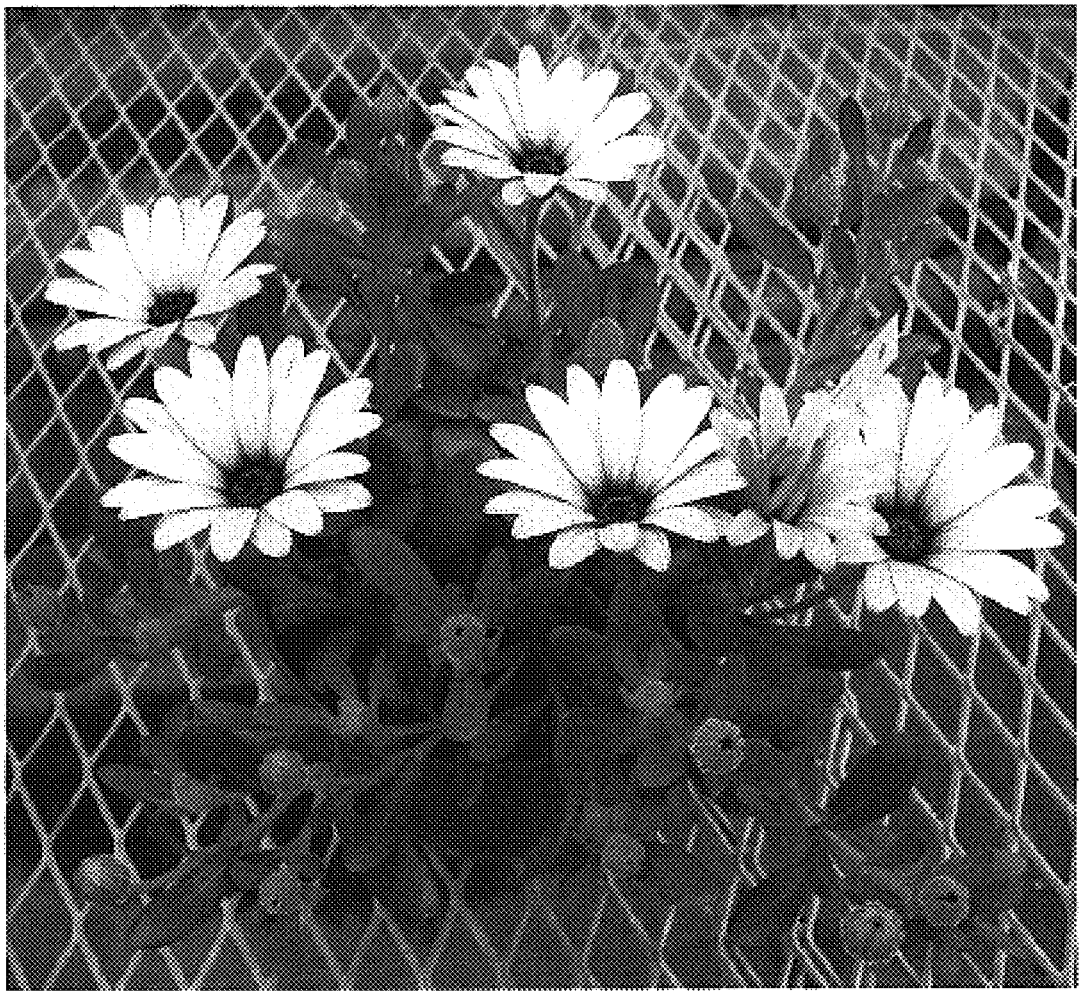

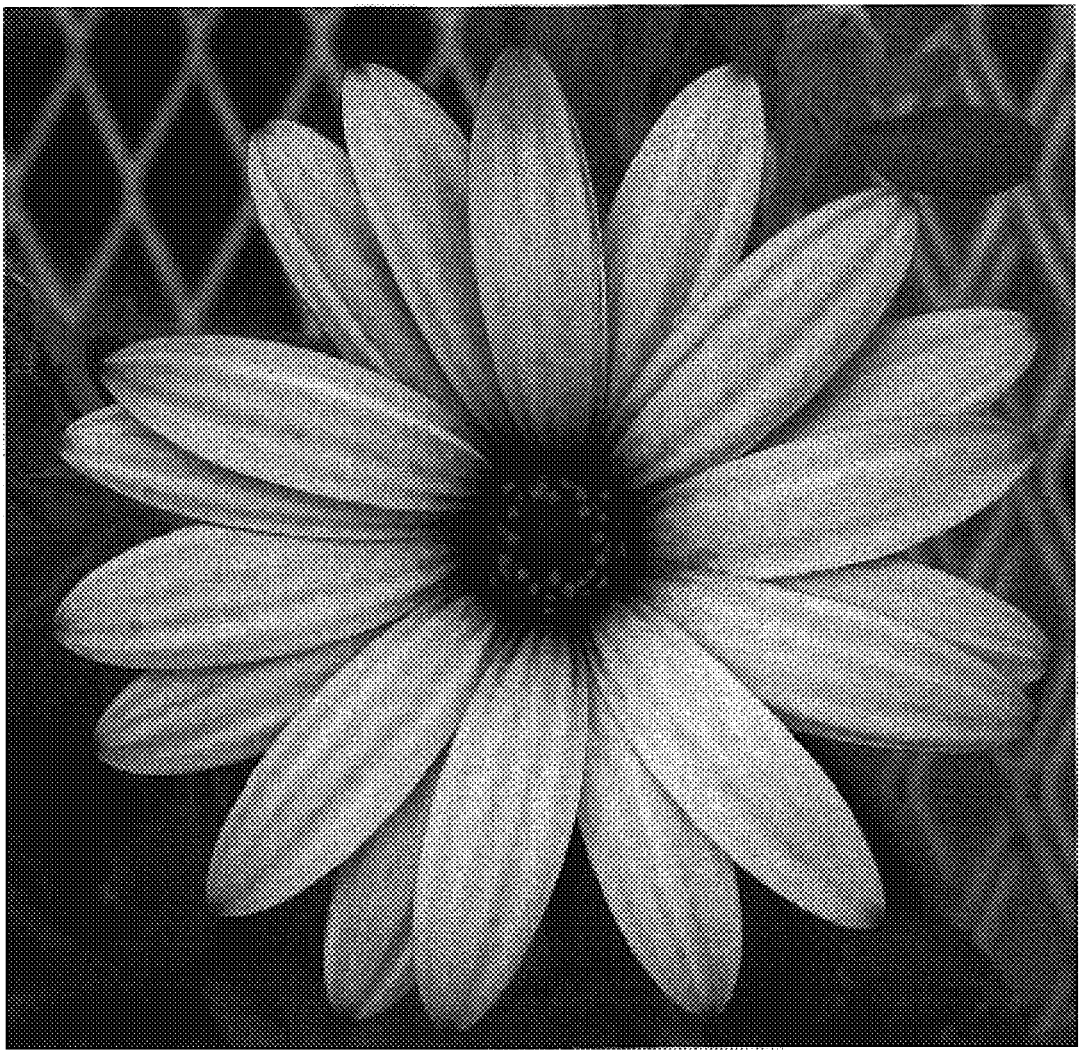

* * * * *